United States Patent [19]

Sasaki et al.

[11] Patent Number: 5,055,593

[45] Date of Patent: Oct. 8, 1991

[54] 1,3-BIS(DICARBOXYPHENYL)-1,1,3,3-TETRAPHENYLDISILOXANE DERIVATIVE, PROCESS FOR PRODUCING THE SAME, AND PROCESS FOR PRODUCING POLYIMIDE FROM THE SAME

[75] Inventors: Akihiro Sasaki; Tohru Kikuchi, both of Hitachi, Japan

[73] Assignee: Hitachi Chemical Company, Ltd., Tokyo, Japan

[21] Appl. No.: 429,082

[22] Filed: Oct. 30, 1989

[30] Foreign Application Priority Data

Nov. 1, 1988 [JP] Japan .................................. 63-276903

[51] Int. Cl.$^5$ ............................................... C07F 7/08
[52] U.S. Cl. ............................................... 549/214
[58] Field of Search ...................................... 549/214

[56] References Cited

U.S. PATENT DOCUMENTS

| | | | |
|---|---|---|---|
| 2,891,981 | 6/1959 | Gainer et al. | 260/448.2 |
| 3,516,964 | 6/1970 | Patterson | 549/215 |
| 3,940,426 | 2/1976 | Itatani et al. | 549/241 |
| 4,370,487 | 1/1983 | Meyer et al. | 549/241 |
| 4,864,027 | 9/1989 | Shubert et al. | 549/214 |

FOREIGN PATENT DOCUMENTS 981824 1/1965 United Kingdom .

OTHER PUBLICATIONS

Journal of Organic Chemistry, vol. 38, No. 25, 1973, pp. 4271–4274.
Houben-Weyl; edition 4, 1980; vol. XIII/5, pp. 34, 45–50, 132–133, 140–141.
Helvetica Chimica Acta, vol. 57, No. 110, Fasc. 4, pp. 1010–1015.
March, Advanced Org. Chem. 3rd Edition, pp. 399–400, 650–651.
Pratt et al, J. Org. Chem., vol. 38, No. 25, 1973, p. 4271.

Primary Examiner—Cecilia Shen
Attorney, Agent, or Firm—Antonelli, Terry, Stout & Kraus

[57] ABSTRACT 1,3-Bis(dicarboxyphenyl)-1,1,3,3-tetraphenyldisiloxane derivatives useful as raw materials of polyimide resins, hardeners for epoxy resins and others and process for producing these derivatives, and polyamic acid and polyamic acid ester, and polyimide resins and processes for producing them from said disiloxane derivatives. The polyimide resins are good in properties such as adhesion to silicon substrates, heat resistance and mechanical properties.

4 Claims, 6 Drawing Sheets

1,3-BIS(DICARBOXYPHENYL)-1,1,3,3-TETRAPHENYLDISILOXANE DERIVATIVE, PROCESS FOR PRODUCING THE SAME, AND PROCESS FOR PRODUCING POLYIMIDE FROM THE SAME

BACKGROUND OF THE INVENTION

1. Field of the Invention

The present invention relates to 1,3-bis-(dicarboxyphenyl)-1,1,3,3-tetraphenyldisiloxane derivatives useful as raw materials of polyimide resins, as hardeners for epoxy resins, and as others. The invention also relates to processes for producing these derivatives, and processes for producing polyimide resins from these derivatives.

2. Description of Prior Art 1,3-Bis(3,4-dicarboxyphenyl)-1,1,3,3-tetramethyldisiloxane dianhydride represented by the formula

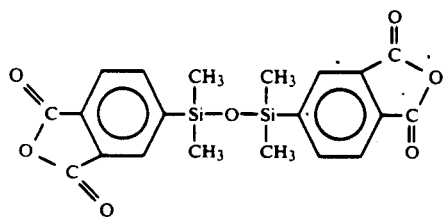

is already known as an aromatic tetracarboxylic dianhydride containing a disiloxane linkage (J. Org. Chem., Vol 38, p. 4271 (1973)).

Properties of polyimides produced from 1,3-bis(3,4-dicarboxyphenyl)-1,1,3,3-tetramethyldisiloxane dianhydride are described on page 51 of POLYIMIDES edited by K.L. Mittal (1984, issued by Plenum Press)

Polyimides produced from aromatic tetracarboxylic dianhydrides and aromatic diamines are known as resins excellent in heat resistance.

However, polyimide resins produced from 1,3-bis(3,4-dicarboxyphenyl)-1,1,3,3-tetramethyldisiloxane dianhydride by combining with aromatic diamines suffer from the problem of lower glass transition temperatures and lower thermal decomposition temperatures than those of other polyimide resins. For example, a polyimide resin from said dianhydride and diaminodiphenyl ether exhibits a glass transition temperature of 164° C. and a thermal decomposition temperture of 398° C.

Such being the case, there has been demand for an aromatic tetracarboxylic dianhydride which has a disiloxane linkage in the molecule and can provide a polyimide having a higher glass transition temperature and a higher thermal decomposition temperature.

SUMMARY OF THE INVENTION

The present invention provides (i) 1,3-bis-(dicarboxyphenyl)-1,1,3,3-tetraphenyldisiloxane derivatives which yield polyimide resins improved in heat resistance as compared with polyimide resins from 1,3-bis(3,4-dicarboxyphenyl)-1,1,3,3-tetramethyldisiloxane dianhydride, (ii) processes for producing those derivatives, and (iii) processes for producing polyimides from those derivatives.

DETAILED DESCRIPTION OF THE INVENTION

The present invention involves a 1,3-bis(dicarboxyphenyl)-1,1,3,3-tetraphenyldisiloxane dianhydride represented by the general formula [I]:

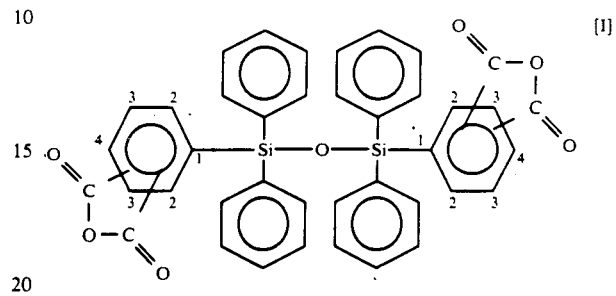

wherein two acid anhydride residues independently of each other are attached to the adjacent phenyl rings at 2,3-positions or 3,4-positions.

Therefore the invention involves isomers represented by the general formula [I], i.e. 1,3-bis-(3,4-dicarboxyphenyl)-1,1,3,3-tetraphenyldisiloxane dianhydride, 1,3-bis(2,3-dicarboxyphenyl)-1,1,3,3-tetraphenyldisiloxane dianhydride, and 1-(2,3-dicarboxyphenyl)-3-(3,4-dicarboxyphenyl)-1,1,3,3-tetraphenyldisiloxane dianhydride. These compounds are useful as intermediates in the production of polyimides.

The invention also involves a 1,3-bis-(dimethylphenyl)-1,1,3,3-tetraphenyldisiloxane represented by the general formula [II]:

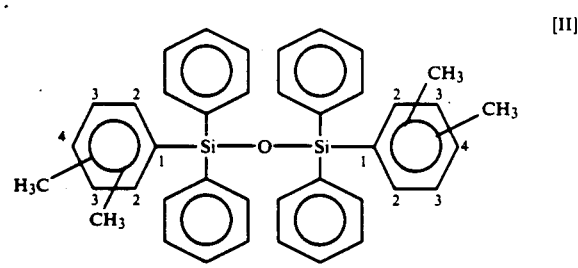

wherein two methyl groups independently of each other are attached to the adjacent phenyl rings at 2,3-positions or 3,4-positions.

Therefore the invention involves isomers represented by the general formula [II], i.e. 1,3bis-(3,4-dimethylphenyl)-1,1,3,3-tetraphenyldisiloxane, 1,3-bis(2,3-dimethylphenyl)-1,1,3,3-tetraphenyldisisiloxane, and 1-(3,4-dimethylphenyl)-3-(2,3-dimethylphenyl)-1,1,3,3-tetraphenyldisiloxane. These compounds are also useful as intermediates in the production of polyimides.

The invention also involves a 1,3-bis-(dicarboxyphenyl)-1,1,3,3-tetraphenyldisiloxane represented by the general formula [III]:

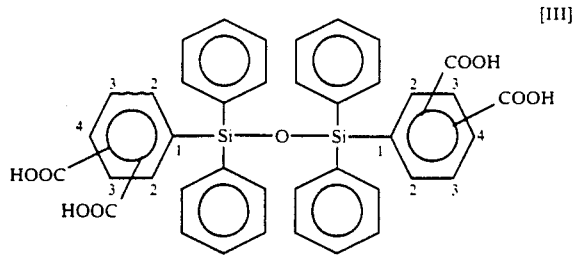

[III]

wherein two carboxy groups independently of each other are attached to the adjacent phenyl rings at 2,3-positions or 3,4-positions.

Therefore the invention involves isomers represented by the general formula [III], i.e., 1,3-bis(3,4-dicarboxyphenyl)-1,1,3,3-tetraphenyldisiloxane, 1,3-bis(2,3-dicarboxyphenyl)-1,1,3,3-tetraphenyldisiloxane, and 1-(2,3-dicarboxyphenyl)-3-(3,4-dicarboxyphenyl)-1,1,3,3-tetraphenyldisiloxane. These compounds are also useful as intermediates in the production of polyimides Further, the invention involves a process (hereinafter referred to as process A) for producing a 1,3-bis(dicarboxyphenyl)-1,1,3,3-tetraphenyldisiloxane dianhydride represented by the general formula [I]:

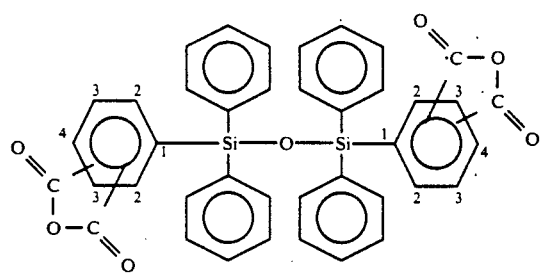

[I]

wherein two acid anhydride residues independently of each other are attached to the adjacent phenyl rings at 2,3-positions or 3,4-positions, the process comprising;

coupling a Grignard reagent of halo-o-xylene with a diphenylhalosilane represented by the general formula [IV]:

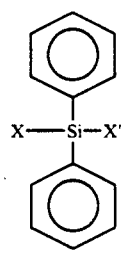

[IV]

wherein X and X' independently of each other denote halogen, to form a diphenyl (dimethyl) halosilane represented by the general formula [V]:

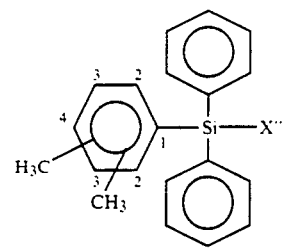

[V]

wherein, two methyl groups are attached to the phenyl ring at 2,3-positions or 3,4-positions and X" is X or X' shown in the above general formula [IV] and denotes halogen;

hydrolyzing the diphenyl (dimethylphenyl) halosilane to form a 1,3-bis(dimethylphenyl)-1,1,3,3-tetraphenyldisiloxane represented by the general formula [II]:

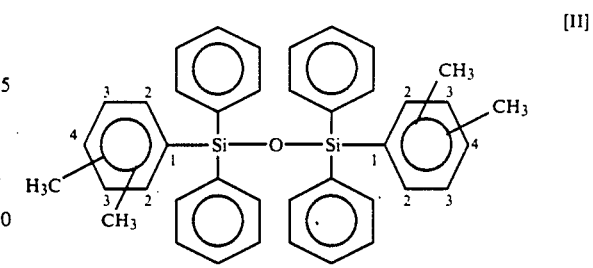

[II]

wherein two methyl groups independently of each other are attached to the adjacent phenyl rings at 2,3-positions or 3,4-positions;

oxydizing the obtained compound that is represented by the general formula [II] to form a 1,3-bis(dicarboxyphenyl)-1,1,3,3-tetraphenyldisiloxane represented by the general formula [III]:

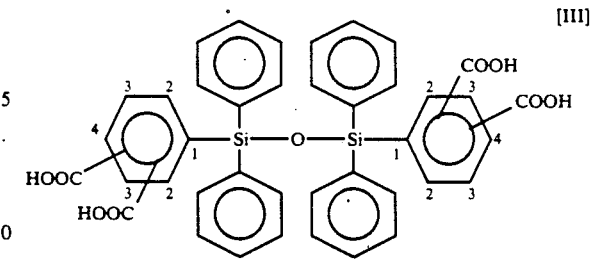

[III]

wherein two groups of carboxy radicals independently of each other are attached to the adjacent phenyl rings at 2,3-positions or 3,4-positions; and subjecting the obtained compound that is represented by the general formula [III] to dehydration ring closure.

The invention also involves a process for producing 1,3-bis(3,4-dicarboxyphenyl)-1,1,3,3-tetraphenydisiloxane dianhydride, which comprising subjecting the product of dehydration ring closure obtained in process A to recrystallization from an ether solvent, aromatic solvent or paraffinic solvent.

The invention also involves a process for producing high-purity 1,3-bis(3,4-dicarboxyphenyl)-1,1,3,3-tetraphenyldisiloxane dianhydride, which comprises subjecting the product of dehydration ring closure obtained in process A to recrystallization from an ether solvent, further subjecting the recovered crystals of 1,3-bis(3,4-dicarboxyphenyl)-1,1,3,3-tetraphenyldisiloxane dianhydride to recrystallization from toluene, and recovering the formed crystals by filtration.

The present invention is described below in detail.

Halo-o-xylenes for use in process A include 4-iodo-o-xylene, 4-bromo-o-xylene, 4-chloro-o-xylene, 3-iodo-o-xylene, 3-bromo-o-xylene, and 3-chloro-o-xylene. These halo-o-xylenes may be used alone or in combination.

The halo-o-xylene can be converted to the Grignard reagent thereof by the ordinary method. For instance, the Grignard reagent can be prepared by using 1.0 gram atom or more of metallic magnesium per 1.0 mole of the halo-o-xylene. When the amount of metallic magnesium used is less than 1.0 gram atom, a part of the halo-o-xylene remains unreacted and in the next coupling step, it reacts with a part of the Grignard reagent of halo-o-xylene, forming tetramethylbiphenyl, which is undesirable. The preparation of the Grignard reagent is carried out between 0° C. and the reflux temperature of the used solvent for a period generally from 1 to 10 hours.

When the amount of metallic magnesium used exceeds 1.0 gram atom per 1.0 mole of the halo-o-xylene, unreacted metallic magnesium remains, which can be removed by filtration. Suitable solvents for use in the reaction include ethyl ether and tetrahydrofuran.

An example of the diphenyldihalosilane represented by the general formula [IV] is diphenyldichlorosilane, the addition of which to the Grignard reagent can promote the coupling reaction.

The diphenyldihalosilane may be used in an amount of 0.5 to 1.5 moles per 1.0 mole of the Grignard reagent of halo-o-xylene. When the amount is less than 0.5 mole, this produces no fundamental adverse effect on the coupling reaction but tends to lower the yield of the reaction product.

When the amount of diphenyldihalosilane used exceeds 1.5 moles, the excess of this compound eventually forms polysiloxane compounds, which are liable to remain as contaminants in the intermediate compound represented by the general formula [II] even after purification thereof.

For the purpose of reducing this disadvantage, the amount of diphenyldihalosilane used is preferably from 0.9 to 1.1 moles, particularly preferably from 0.95 to 1.0 mole, per 1.0 mole of the Grignard reagent of halo-o-xylene.

The coupling reaction is carried out at a temperature desirably from 20 to 60° C. for a period generally from 1 to 5 hours. At low reaction temperatures, the reaction period is prolonged but no fundamental problem arises. At higher reaction temperatures than 60° C., high-boiling by-products such as polysiloxane compounds tend to form in larger amounts.

After completion of the coupling reaction, the formed diphenyl (dimethylphenyl)halosilane represented by the general formula [V] can be converted to a 1,3-bis(dimethylphenyl)-1,1,3,3-tetraphenyldisiloxane represented by the general formula [II] by adding at least one mole of water per one mole of the silane derivative as it is without taking it out of the reaction vessel or after the silane derivative has been taken out. It is preferable in this case to add a large excess of water to the diphenyl (dimethylphenyl) halosilane. This is for the purpose of dissolving the magnesium halide formed by the coupling reaction in excess water and separating the resulting aqueous solution from the organic layer, thereby facilitating the removal of magnesium halide. The hydrolysis is generally accomplished at a temperature of 10 to 50° C.: for instance, at room temperature, the reaction proceeds sufficiently with stirring for a period of 10 minutes to 1 hour.

After completion of the reaction, the organic layer that is a product solution in ether, tetrahydrofuran, or the like, is washed with water to remove the magnesium halide completely and a 1,3-bis(dimethylphenyl)-1,1,3,3-tetraphenyldisiloxane represented by the general formula [II] can be obtained from the washed organic layer.

Then a 1,3-bis(dicarboxyphenyl)-1,1,3,3-tetraphenyldisiloxane represented by the general formula [III], which is a silicon-containing tetracarboxylic acid pertaining to the present invention, can be produced by oxidizing the above obtained 1,3-bis-(dimethylphenyl)-1,1,3,3-tetraphenyldisiloxane.

Available methods for this oxidation include, for example, a liquid-phase autooxidation method using oxygen or air in the presence of an organic cobalt catalyst and an oxidation method using a permanganate.

Organic cobalt compounds useful as catalysts in the liquid-phase autooxidation method are such as cobalt naphthenate and cobalt octenate. The catalyst is used in an amount of 1 to 5 mole% based on the 1,3-bis(dimethylphenyl)-1,1,3,3-tetraphenyldisiloxane.

An aliphatic carboxylic acid such as acetic acid or propionic acid may be used as a solvent in this reaction. Further, an alkali metal halide such as sodium bromide, sodium chloride, or potassium bromide may be used as a co-catalyst in an amount of 1 to 5 mole% based on the above derivative. The reaction can be carried out at a temperature of 150 to 230° C. and a pressure of 5 to 50 kg/cm$^2$. After completion of the reaction, a solvent such as toluene, ethyl ether, or isopropyl ether is added to extract the reaction product into the solvent layer. This solvent layer is taken out and washed with water to remove the aliphatic carboxylic acid used as a reaction solvent and the co-catalyst. Then the 1,3-bis(dicarboxyphenyl)-1,1,3,3-tetraphenyldisiloxane can be obtained by evaporating the solvent away.

A permanganate such as potassium permanganate may be used in another oxidation method mentioned above. Suitable solvents for use in this case include mixtures of water with individual organic solvents such as pyridine, dioxane, and t-butanol. In the water-pyridine mixture, the weight ratio of pyridine to water is desired to be 0.5–3.0:1.0. For instance, to 100 g of the water-organic solvent mixture are added 2–15 g of the 1,3-bis(dimethylphenyl)-1,1,3,3-tetraphenyldisiloxane and then gradually potassium permanganate in a molar ratio of 12 to the disiloxane derivative. When this molar ratio is less than 12, the oxidation yield tends to be unsatisfactory. The reaction is conducted between 50° C. and the reflux temperature for a period generally from 5 to 10 hours. Potassium permanganate is converted by this reaction into manganese oxide, which, insoluble in the solvent mixture, can be removed by filtration. Since the 1,3-bis(dicarboxyphenyl)-1,1,3,3-tetraphenyldisiloxane in the form of potassium salt is dissolved in the filtrate that contains the abovementioned organic solvent, the disiloxane derivative is precipitated by adding concentrated hydrochloric acid after the organic solvent has been evaporated away. The amount of conc. hydrochloric acid to add is such that the pH of the aqueous solution may become 1, whereby the 1,3-bis(dicarboxyphenyl)-1,1,3,3-tetraphenyldisiloxane can be obtained.

The corresponding dianhydride can be produced from the thus obtained 1,3-bis(dicarboxyphenyl)-1,1,3,3tetraphenyldisiloxane by heating it at a temperature of 100 to 200° C. under a reduced pressure of 0.1 to 50 mmHg for a period of 2 to 10 hours or by dissolving it in acetic anhydride, refluxing the solution, and evaporating away the acetic anhydride and the formed acetic acid.

When the halo-o-xylene used is a mixture of 4-halo-o-xylene and 3-halo-o-xylene, the dianhydride obtained as described above is a mixture of 1-(2,3-dicarboxyphenyl)-3-(3,4-dicarboxyphenyl)-1,1,3,3-tetraphenyldisiloxane dianhydride, 1,3-bis(3,4-dicarboxyphenyl)-1,1,3,3-tetraphenyldisiloxane dianhydride, and a trace of 1,3-bis(2,3-dicrboxyphenyl)-1,1,3,3-tetraphenyldisiloxane dianhydride.

From this mixture, white crystals of 1,3-bis(3,4-dicarboxyphenyl)-1,1,3,3-tetraphenyldisiloxane dianhydride can be obtained by separation through recrystallization from a solvent selected from the group consisting of; ethers such a ethyl ether and diisopropyl ether; aromatic solvents such as toluene and xylene; mixtures of toluene and ethers; and mixtures of toluene and paraffinic solvents such as n-hexane and ligroin. The purity of white crystals obtained is from 97 to 99 mole%.

An example of other methods for recovering 1-bis(3,4-dicarboxyphenyl)-1,1,3,3-tetraphenyldisiloxane dianhydride of high purity (at least 99.5 mole%) comprises heating the above obtained mixture of dianhydrides in about 1.5 times the mixture weight of an ether at about 30° C. with stirring to give a uniform solution, allowing it to stand for 1–2 hours at normal temperature to precipitate crystals, then heating the recovered crystals in an aromatic solvent such as toluene at about 80–100° C. to give a uniform solution, allowing it to stand for 1–2 hours at normal temperature, and filtering the precipitated crystals. It is effective for raising the purity to repeat several times the recrystallization from an aromatic solvent such as toluene. The dianhydride of high purity is advantageous in that its reactions with diamines can yield polyamide acids of higher molecular weights.

The present invention also involves a process for producing a polyimide having constitutional units represented by the general formula [X]:

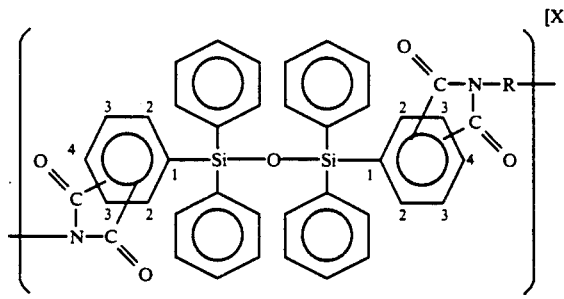

wherein, two dibasic acid anhydride residues independently of each other are attached to the adjacent phenyl rings at 2,3-positions or 3,4-positions and R denotes a divalent organic residue, the process comprising reacting a 1,3-bis(dicarboxyphenyl)-1,1,3,3-tetraphenyldisiloxane dianhydride with a diamine represented by the general formula [IX]:

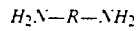   [IX]

wherein R is as defined above.

The present invention further involves a process for producing a polyimide having constitutional units represented by the general formula [XI]:

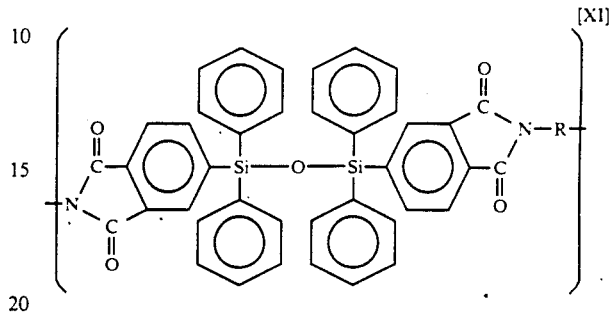

wherein R denotes a divalent organic residue, the process comprising reacting 1,3-bis(3,4-dicarboxyphenyl)-1,1,3,3-tetraphenyldisiloxane dianhydride with a diamine represented by the general formula [IX]:

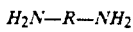   [IX]

wherein R is as defined above.

The above productions of polyimides can be carried out, for instance, as follows:

A diamine represented by the general formula [IX] is dissolved in an inert solvent, an acid anhydride containing a 1,3-bis(dicarboxyphenyl)-1,1,3,3-tetraphenyldisiloxane dianhydride or 1,3-bis(3,4-dicarboxyphenyl)-1,1,3,3-tetraphenyldisiloxane dianhydride is added to the solution, and the mixture is stirred while maintaining it at room temperature or below. Thereupon the reaction proceeds quickly and the viscosity of reaction mixture rises gradually, whereby a polyamic acid can be produced.

Thereafter the dehydration ring closure of the polyamide acid is caused by heating it or treating it with acetic anhydride or the like. Thus a polyimide having constitutional units represented by the general formula [X] or [XI] can be obtained.

Diamines represented by the general formula [IX] include aromatic diamines, e.g. 4,4'-diaminodiphenyl ether, 4,4'-diaminodiphenylmethane, 4,4'-diaminodiphenyl sulfone, 4,4'-diaminodiphenyl sulfide, benzidine, m-phenylenediamine, p-phenylenediamine, 2,2-bis(4-aminophenyl)propane, diaminobenzophenone, 1,5-diaminonaphthalene, 2,6-diaminonaphthalene, 1,3-bis(4-aminophenoxy)benzene, 1,4-bis(4-aminophenoxy)benzene, 4,4'-di(4-aminophenoxy)diphenyl sulfone, 4,4'-di(-3aminophenoxy)diphenyl sulfone, 2,2-bis[4-(4-aminophenoxy)phenyl]propane, 4,4''-diamino-p-terphenyl 2,2-bis(4-aminophenyl)hexafluoropropane 2,2-bis(3-aminophenyl)hexafluoropropane 2,2-bis[4-(4-aminophenoxy)phenyl]hexafluoropropane and 2,2-bis[4-(3-aminophenoxy)phenyl]hexafluoropropane.

It is also possible to use amines such as ethylenediamine, 1,3-propanediamine, tetramethylenediamine, pentamethylenediamine, hexamethylenediamine, heptamethylenediamine, octamethylenediamine, 1,4-diaminocyclohexane, 1,2-bis(4-aminophenoxy)ethane, bis[2-(4-aminophenoxy)ethyl] ether, 1,2-bis[2-(4-aminophenoxy)ethoxy]ethane, bis{2-[2-(4-aminophenoxy)e- thoxy]ethyl} ether, 4,4'-diaminodiphenyl ether-3-sulfoneamide, 3,4'-diaminodiphenyl ether-4-sulfoneamide, 3,4'-diaminodiphenyl ether-3'-sulfoneamide, 3,3'-diaminodiphenyl ether-4-sulfoneamide, 4,4'-diaminodiphenylmethane-3-sulfoneamide, 3,4'-diaminodiphenylmethane-4-sulfoneamide, 3,4'-diaminodiphenylmethane-3'-sulfoneamide, 3,3'-diaminodiphenylmethane-4-sulfoneamide, 4,4'-diaminodiphenylsulfone-3-sulfoneamide, 3,4'-diaminodiphenylsulfone-4-sulfoneamide, 3,4'-diaminodiphenylsulfone-3'-sulfoneamide, 3,3'-diaminodiphenylsulfone-4-sulfoneamide, 4,4'-diaminodiphenylsulfide-3-sulfoneamide, 3,4'-diaminodiphenylsulfide-4-sulfoneamide, 3,3'-diaminodiphenyhlsulfide-4-sulfoneamide, 3,4'-diaminodiphenylsulfide-3'-sulfoneamide, 1,4-diaminobenzene-2-sulfoneamide, 4,4'-diaminodiphenyl ether-3-carbonamide, 3,4'-diaminodiphenyl ether-4-crbonamide, 3,4'-diaminodiphenyl ether-3'-carbonamide, 3,3'-diaminodiphenyl ether-4-carbonamide, 4,4'-diaminodiphenylmethane-3-carbonamide, 3,4'-diaminodiphenylmethane-4-carbonamide, 3,4'-diaminodiphenylmethane-3'carbonamide, 3,3'-diaminodiphenylmethane-4-carbonamide,, 4,4'-diaminodiphenylsulfone-3-carbonamide, 3,4'-diaminodiphenylsulfone-4-carbonamide, 3,4'-diaminodiphenylsulfone-3'-carbonamide, 3,3'-diaminodiphenylsulfone-4carbonamide, 4,4'-diaminodiphenylsulfide-3-carbonamide, 3,4'-diaminodiphenylsulfide-4-carbonamide, 3,3'-diaminodiphenylsulfide-4-carbonamide, 3,4'-diaminodiphenylsulfide-3'-sulfoneamide, 1,4-diaminobenzene-2-carbonamide, etc. From the viewpoint of improving heat resistance, the use of aromatic diamines and diaminoamide compounds is preferable.

In order to improve the adhesive properties of the orientation film in the liquid crystal display device, it is preferable to co-use diaminosiloxane represented by the formula [XIII],

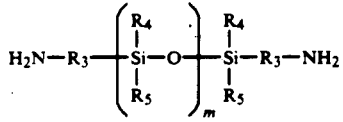

[XIII]

wherein $R_3$ is a bivalent aliphatic or aromatic hydrocarbon group preferably having 3 to 8 carbon atoms such as a propylene group, a phenylene group, etc ; $R_4$ and $R_5$ are independently a monovalent hydrocarbon group having 1 to 6 carbon atoms such as an alkyl group preferably having 1 to 6 carbon atoms, a phenyl group, etc.; and m is an integer of 1 or more.

Examples of the diaminosiloxane of the formula [XIII] are as follows:

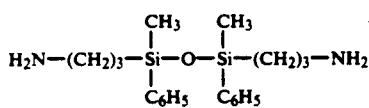

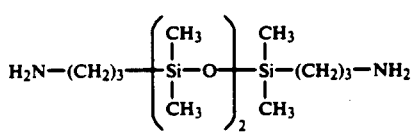

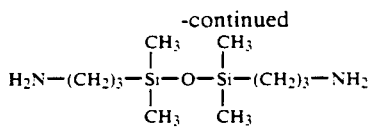

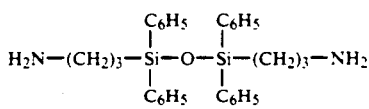

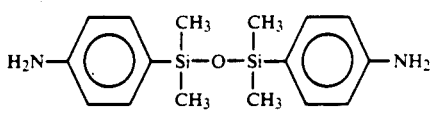

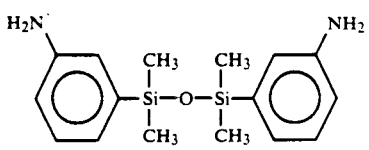

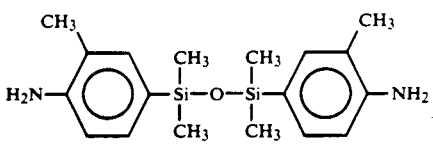

Jointly with the 1,3-bis(dicarboxyphenyl)-1,1,3,3-tetraphenyldisiloxane dianhydride, it is possible to use other acid dianhydrides such as benzophenonetetracarboxylic dianhydride and pyromellitic dianhydride.

Suitable inert solvents for use in the polyamide acid forming reaction include, for example, N-methyl-2-pyrrolidone, N,N-dimethylacetamide, N,N-dimethylformamide, dimethylesulfoxide, hexamethylphosphoramide, tetramethylene sulfone, p-chlorophenol, p-bromophenol, and 2-chloro-4-hydroxytoluene.

The following examples illustrate the present invention.

EXAMPLES

EXAMPLE 1

(1) Preparation of Grignard Reagent

A 2-liter, 4-necked flask equipped with an Allihn condenser, dropping funnel, thermometer, and stirrer was dried sufficiently with argon gas and then charged with 100 ml of tetrahydrofuran dehydrated with metallic sodium, 9.72 g of metallic magnesium, and 10.0 g of bromo-o-xylene (a mixture of 4-bromo-o-xylene and 3-bromo-o-xylene in 75:25 ratio). Over 1 hour from the time this reaction liquid began to cloud indicating the start of Grignard reagent formation, a mixture of 64.0 g of the same bromo-o-xylene as stated above and 100 ml of tetrahydro-furan was added dropwise from the dropping funnel. During this dropping, the reaction temperature was kept at 40° C. by cooling with an ice-bath, since this reaction is exothemic. After the dropping had been finished, the reaction mixture, in which metallic magnesium still remained, was heated with stirring on an oil bath at 40° C. for 5 hours to convert metallic magnesium completely to the Grignard reagent.

(2) Coupling Reaction

To the resulting mixture was added dropwise 101.28 g (0.40 mole) of diphenyldichlorosilane from the dropping funnel in 20 minutes. The reaction temperature was kept at 20° C. during this dropping and then for 5 hours to complete the coupling reaction.

(3) Hydrolysis

20 The formed diphenyl(dimethylphenyl)-chlorosilane (isomeric mixture), as such without being taken out of the flask, was subjected to the next reaction.

That is, 300 ml of toluene was added to the product mixture of coupling reaction and then 250 ml of water deionized by ion exchange was added gradually over 1 hour while stirring The lower layer, that is, an aqueous solution, was removed by using a separating funnel. The upper layer, i.e. a product solution in tetra-hydrofuran and toluene, was washed three times with 100 ml each of an aqueous solution of 2 wt% of sodium carbonate, and freed from the solvents in an evaporator, giving 118 g of crystals of crude 1,3-bis(dimethylphenyl)-1,1,3,3-tetraphenyldisiloxone (isomeric mixture).

These crystals were subjected to recrystallization from 177 g of n-hexane, yielding 40 g of 1,3-bis(dimethylphenyl)-1,1,3,3-tetraphenyldisiloxane (isomeric mixture) of 98 mole% purity [analyzed with a DSC (Model 910, supplied by Du Pont de Nemours, E.I., & Co.)].

(4) Oxidation

Then 23.6 g (40 m moles) of the above obtained disiloxane derivative, 240 ml of pyridine, and 120 of water deionized by ion exchange were charged into a 1liter, 4-necked flask equipped with an Allihn condenser, thermometer, and stirrer, and were heated to 85° C. After gradual addition of 75.9 g (480 m moles) of potassium permanganate to the mixture over 2 hours, stirring was further continued for 4 hours at 85° C. The formed precipitate of manganese oxide was filtered off, pyridine was evaporated away from the filtrate by using a rotary evaporator, and upon addition of 36% hydrochloric acid to the residue, a white resinous precipitate appeared At this time the pH of the aqueous layer was 1. The precipitate was dissolved in a solvent mixture of 220 ml tetrahydrofuran and 150 ml toluene, the solution was washed four times with 75 ml each of a 10% aqueous sodium chloride solution, and the solvent was evaporated from the washed solution in a rotary evaporator, yielding 17.2 g (24.1 m moles) of a pale yellow-brown, resinous tetracarboxylic acid (isomeric mixture).

(5) Dehydration Ring Closure

Then 14.2 g (20 m moles) of the above resinous tetracarboxylic acid, placed in a 100-ml eggplant-shaped flask, was subjected to dehydration ring closure by heating at 180° C. for 3 hours under a reduced pressure of 10 mmHg. The obtained dianhydride was resinous and the yield thereof was 12.8 g (19 m moles).

This product was confirmed to be an anhydride from the result of proton NMR analysis that no absorption by the proton of carboxylic acid was observed in weak magnetic fields of 10 to 13 ppm.

The obtained dianhydride was a mixture containing 1-(2,3-dicarboxyphexyl)-3-(3,4-dicarboxy-phenyl)-1,1,3,3-tetraphenyldisiloxane dianhydride and 1,3-bis(3,4-dicarboxyphenyl)-1,1,3,3-tetraphenyldisiloxane dianhydride as main components and a trace of 1,3-bis(2,3-dicarboxyphenyl)-1,1,3,3-tetraphenyldisiloxane dianhydride.

(6) Preparation of High-purity 1,3-bis(3,4-dicarboxyphenyl)-1,1,3,3-tetraphenyldisiloxane dianhydride In a 100-ml eggplant-shaped flask was placed 10.0 g of the resinous dianhydride obtained in above (5), and was added 20 g of ethyl ether. The mixture was heated under reflux to dissolve the dianhydride, and hot-filtered to remove foreign matter such as dust. Upon cooling the filtrate, white crystals precipitated. Further, these crystals were dissolved in 20 g of toluene by heating it under reflux. The resulting solution was hot-filtered to remove foreign matter such as dust, and the filtrate was cooled to precipitate white crystals. These crystals were filtered off and dried. The yield of these crystals was 3.6 g and the melting point was 185–186° C.

A $^1$H-NMR spectrum, $^{13}$C-NMR spectrum, and infrared absorption spectrum of these crystals are shown in FIGS., 1, 2, and 3, respectively.

Elementary analysis,

Found (%): C, 71.00; H, 3.95

Calcd. (%): C, 71.20; H, 3.88

From the result of these analyses, the obtained crystals were confirmed to be of 1,3-bis(3,4-dicarboxyphenyl)-1,1,3,3-tetraphenyldisiloxane dianhydride.

The purity of these crystals were determined as 99.6 mole% from the result of calorimetry by using a DSC (Model 910, supplied by Du Pont Co.)

EXAMPLES 2

A 200-ml, 3-necked flask equipped with a stirrer was charged with 10.0 g (14.8 m moles) of high-purity 1,3-bis(3,4-dicarboxyphenyl)-1,1,3,3-tetraphenyldisiloxane dianhydride obtained in Example 1, 2.96 g (14.8 m moles) of 4,4'-diaminodiphenyl ether, and 73.5 g of N-methylpyrrolidone as a reaction solvent. The mixture was stirred at 25° C. for 8 hours under a nitrogen atmosphere, yielding a polyamide acid (nonvolatile matter content 15 wt%).

The viscosity of this polyamic acid was 5 poises at 25° C. This polyamide acid was poured and spread on a glass plate, and heated successively at 100° C. for 1 hour, at 200° C. for 1 hour, and at 275° C. for 1 hour to remove the reaction solvent and simultaneously to undergo dehydration ring closure, forming a 30-μm thick polyimide film.

The glass transition temperature of this polyimide film was 188° C. as measured with a DSC (Model 910, supplied by Du Pont Co.) and the 1-% weight loss temperature of the film was 442° C. as measured with the same TGA (Model 951, supplied by Du Pont Co.) (in the air, at a heating rate of 5° C./min).

COMPARATIVE EXAMPLE 1

In the same manner as in Example 2, a polyamide acid (nonvolatile matter content 15 wt%) was prepared by reacting 10.0 g (23.4 m moles) of 1,3-bis(3,4-dicarboxyphenyl)-1,1,3,3-tetramethyldisiloxane dianhydride with 4.69 g (23.4 m moles) of 4.4'-diaminodiphenyl ether in 83.2 g of N-methylpyrrolidone. The viscosity of polyamide acid in the course of this reaction was 3000 poises (at 25° C.).

According then to the procedure of Example 2, a polyimide film was prepared from the obtained polyamide acid and the heat resistance of the film was evaluated. The found glass transition temperature and 1-% weight loss temperature were 164° C. and 419° C., respectively.

EFFECT OF THE INVENTION

The present inventive 1,3-bis(dicarboxyphenyl)-1,1,3,3-tetraphenyldisiloxane dianhydride is a novel compound and useful as a hardener for epoxy resins and as a raw material of polyimide resins. Polyimide resins from the present dianhydride are good in properties such as adhesion to silicon substrates and the like, heat resistance, and mechanical properties. Polyamic acids from the present dianhydride are superior in solubilities in solvents (N-methyl-2-pyrrolidone, tetrahydrofuran, diglyme, dioxane, etc.) and films can be formed very easily from these polyamic acids.

Figure 1:
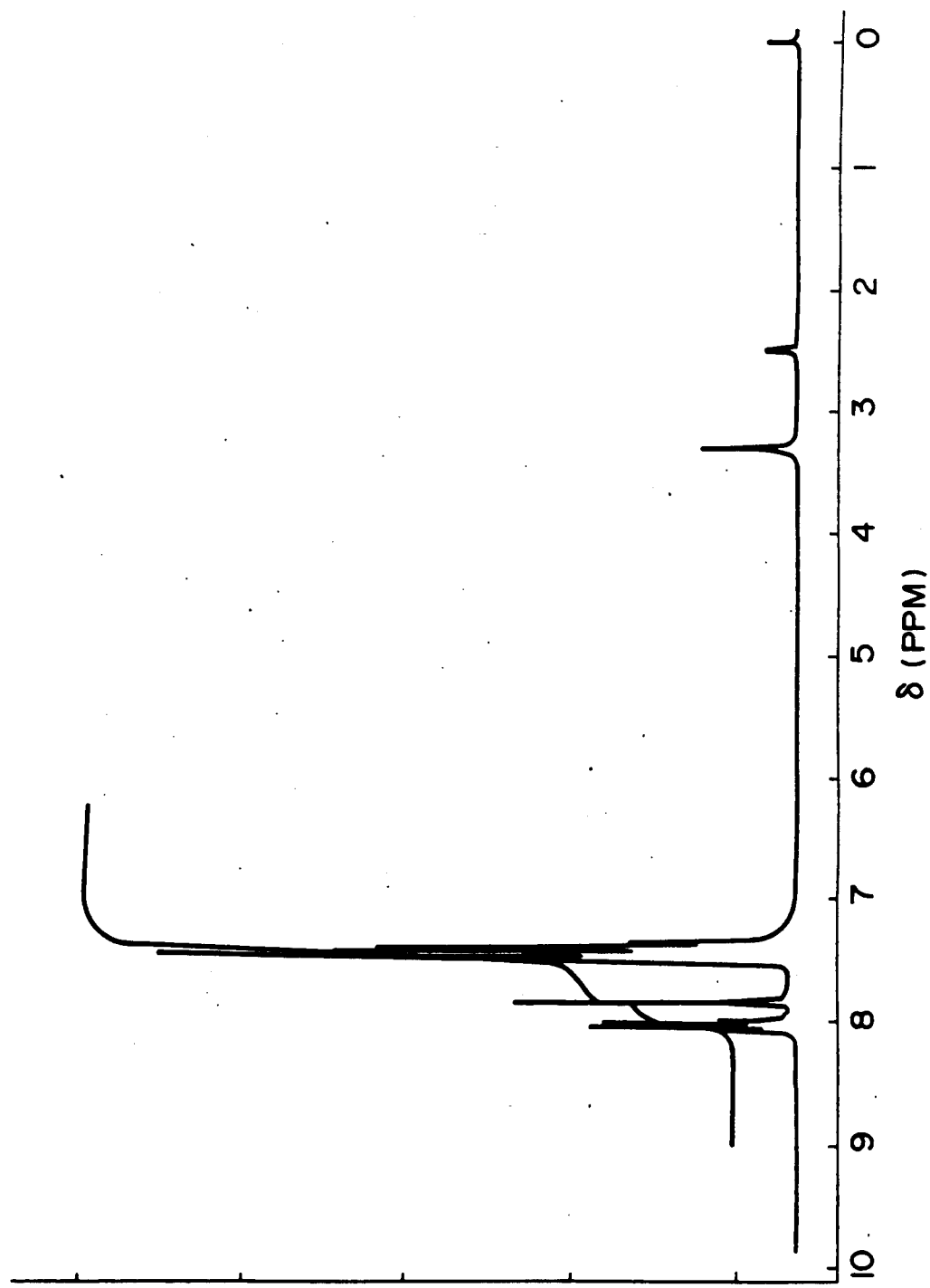
FIGS. 1, 2, and 3 are a $^1$H-NMR spectrum, $^{13}$C-NMR spectrum, and infrared absorption spectrum, respectively, of 1,3-bis(3,4-dicarboxyphenyl)-1,1,3,3-tetraphenyldisiloxane dianhydride.
Figure 2:
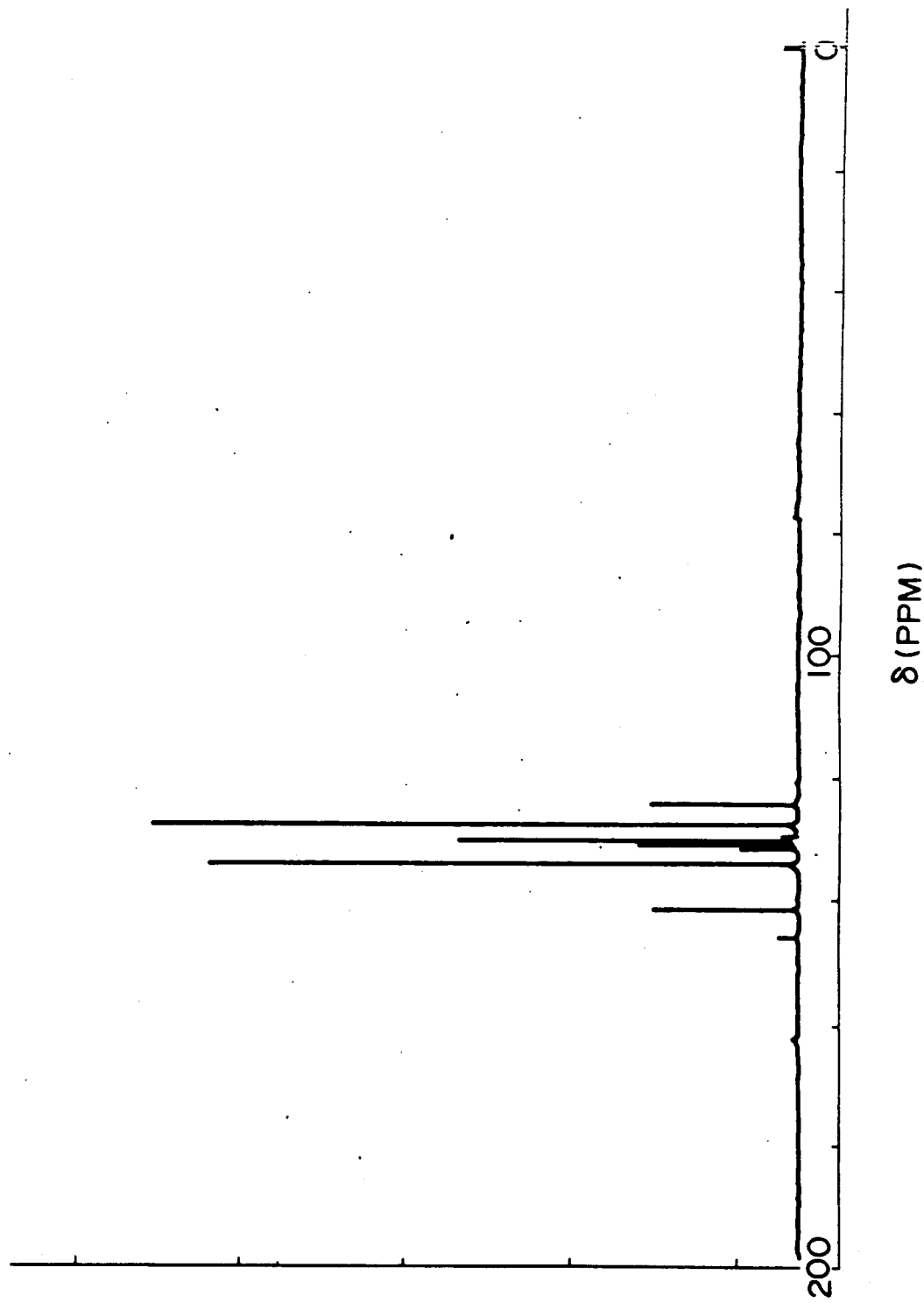
Figure 3:
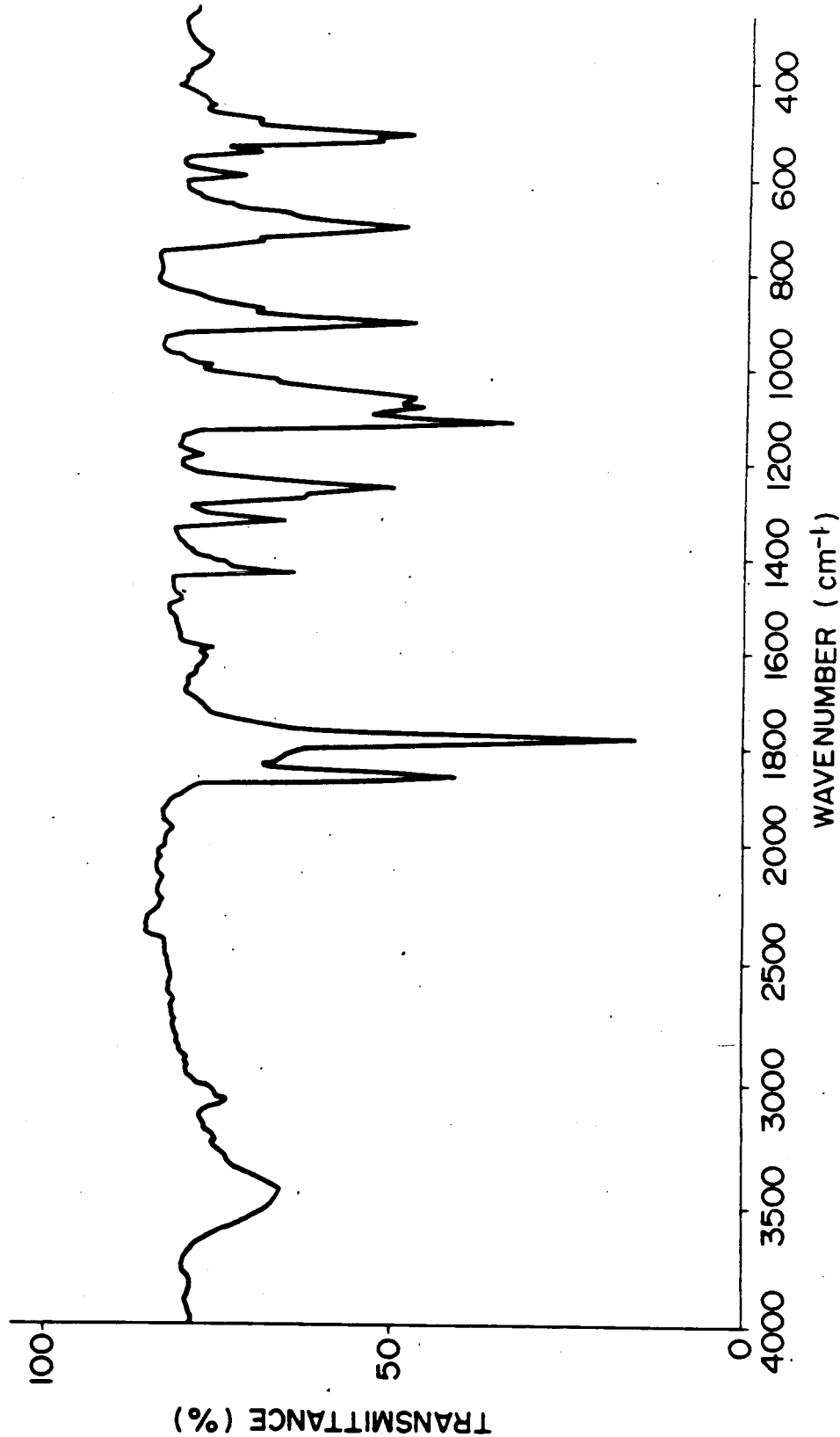
Figure 4:
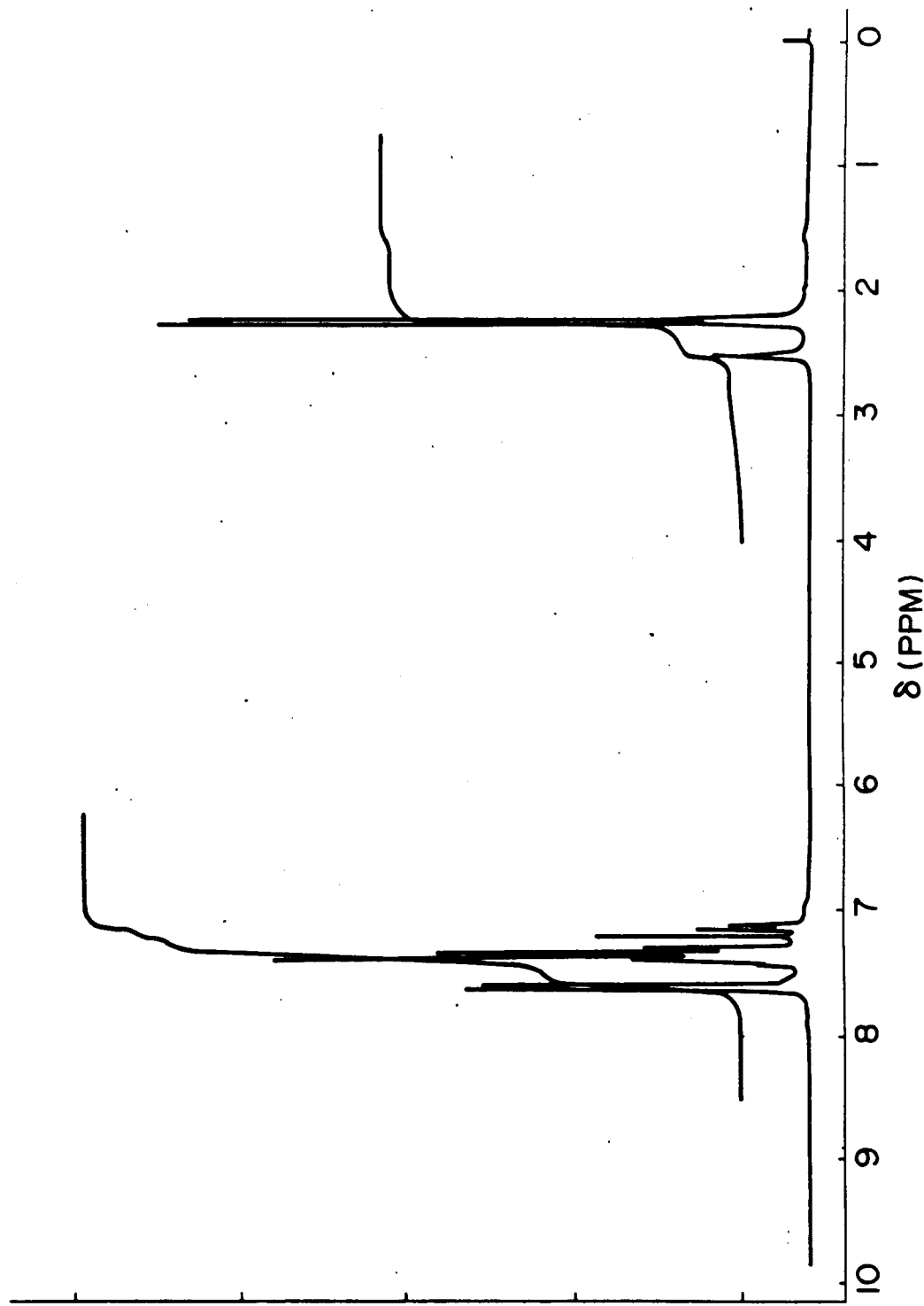
FIGS. 4, 5, and 6 are a $^1$H-NMR spectrum, $^{13}$C-NMR spectrum, and infrared absorption spectrum, respectively, of 1,3-bis(dimethylphenyl)-1,1,3,3-tetraphenyldisiloxane.
Figure 5:
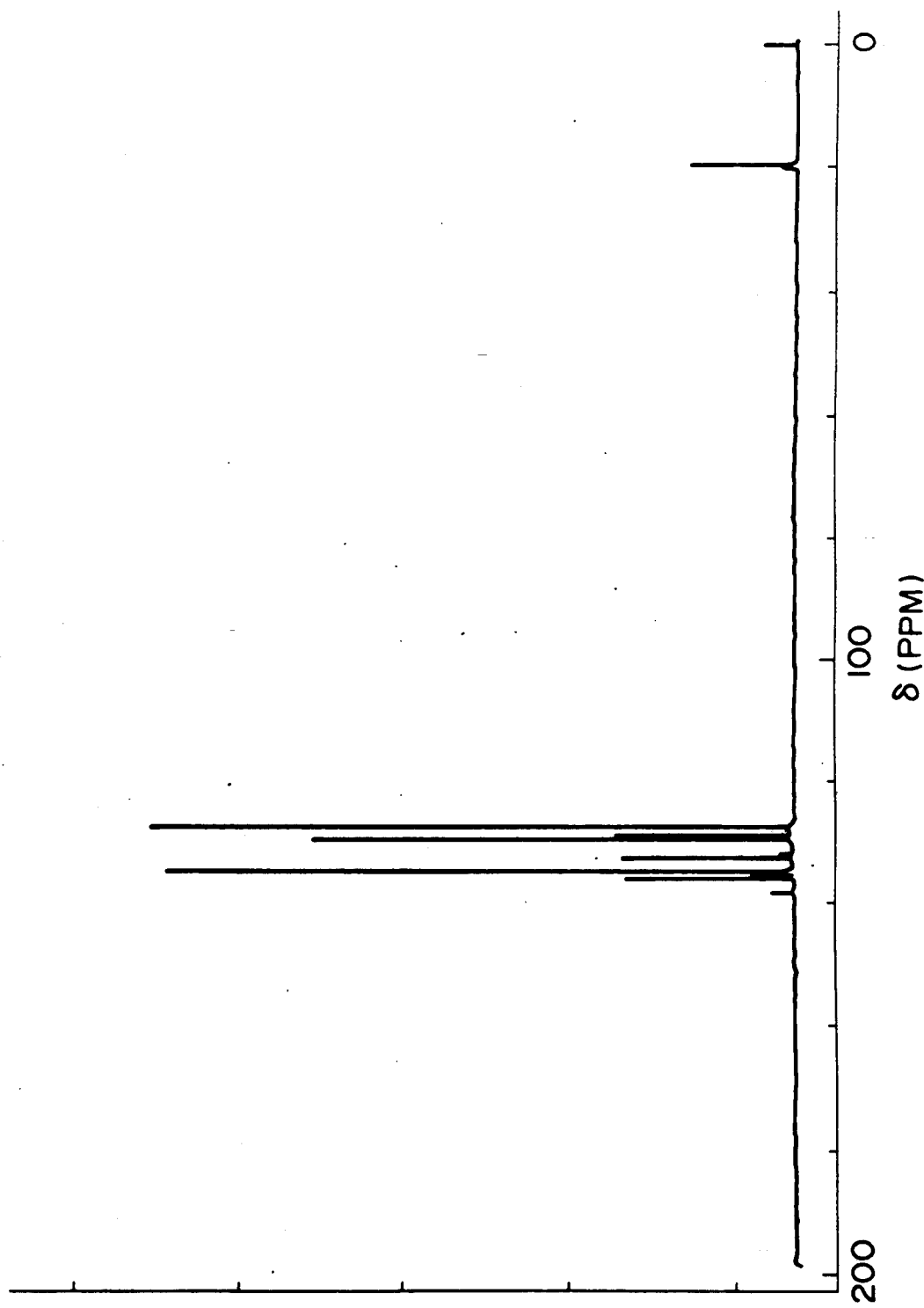
Figure 6:
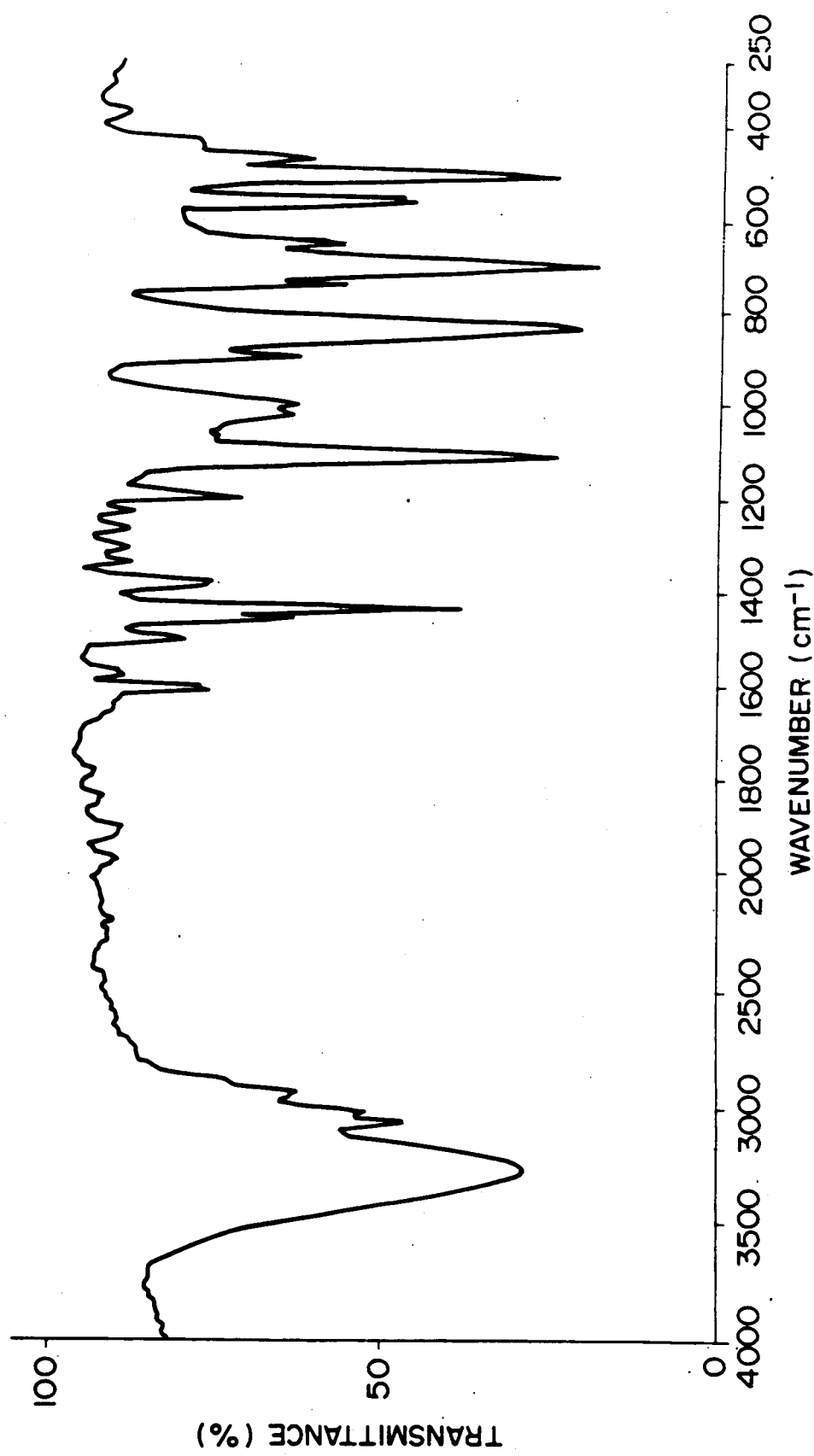

What is claimed is:

1. A 1,3-bis(dicarboxyphenyl)-1,1,3,3-tetraphenyldisiloxane dianhydride represented by the general formula [I]:

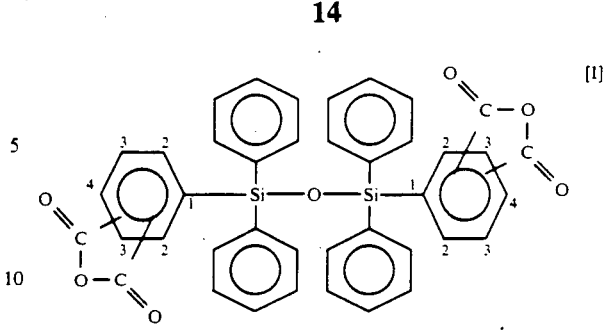

wherein two acid anhydride residues independently of each other are attached to the adjacent phenyl rings at 2,3-positions or 3,4-positions.

2. 1,3-Bis(3,4-dicarboxyphenyl)-1,1,3,3-tetraphenyldisiloxane dianhydride.

3. 1,3-Bis(2,3-dicarboxyphenyl)-1,1,3,3-teetraphenyldisiloxane dianhydride.

4. 1-(2,3-Dicarboxyphenyl)-3-(3,4-dicarboxyphenyl)-1,1,3,3-tetraphenyldisiloxane dianhydride.

* * * * *